(12) United States Patent
Hourmand et al.

(10) Patent No.: US 10,653,851 B2
(45) Date of Patent: May 19, 2020

(54) AUTOINJECTOR WITH AN INNER PLUNGER WHICH DISENGAGES THE OUTER PLUNGER TO RETRACT THE SYRINGE CARRIER

(71) Applicant: SANOFI-AVENTIS DEUTSCHLAND GMBH, Frankfurt am Main (DE)

(72) Inventors: Yannick Hourmand, Haslingfield (GB); Simon Brereton, Cambridgeshire (GB); Thomas Mark Kemp, Ashwell (GB); Rosie Burnell, Cambridge (GB); Matthew Ekman, Cheshire (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 365 days.

(21) Appl. No.: 15/821,166

(22) Filed: Nov. 22, 2017

(65) Prior Publication Data
US 2018/0093046 A1    Apr. 5, 2018

Related U.S. Application Data

(63) Continuation of application No. 14/366,868, filed as application No. PCT/EP2012/076097 on Dec. 19, 2012, now Pat. No. 9,827,381.

(30) Foreign Application Priority Data

Dec. 21, 2011 (EP) ...................... 11194775

(51) Int. Cl.
*A61M 5/32* (2006.01)
*A61M 5/20* (2006.01)

(52) U.S. Cl.
CPC .......... *A61M 5/326* (2013.01); *A61M 5/2033* (2013.01); *A61M 2005/206* (2013.01); *A61M 2005/2013* (2013.01)

(58) Field of Classification Search
CPC .......... A61M 5/2033; A61M 2005/206; A61M 5/326; A61M 5/3202
(Continued)

(56) References Cited

U.S. PATENT DOCUMENTS

2013/0131595 A1* 5/2013 Ekman ................ A61M 5/1452
604/117

FOREIGN PATENT DOCUMENTS

CN         101678167       3/2008
DE       102007013836      9/2008
(Continued)

OTHER PUBLICATIONS

Chinese Search Report in Chinese Application No. 201280069210.5, dated Oct. 23, 2015, 2 pages.
(Continued)

*Primary Examiner* — Phillip A Gray
(74) *Attorney, Agent, or Firm* — Fish & Richardson P.C.

(57) ABSTRACT

Described is an autoinjector comprising a case, a chassis slidably arranged in the case, a syringe carrier operably coupled to the chassis, an outer plunger selectively engaged to the chassis, an inner plunger selectively engaged to the outer plunger, and a drive spring applying a biasing force to the outer plunger. The biasing force is applied to the inner plunger when the inner plunger is engaged to the outer plunger. Rotation of the chassis causes the inner plunger to rotate relative to the outer plunger and disengage the outer plunger to remove the biasing force from the drive spring on the inner plunger. When the inner plunger disengages the outer plunger, the biasing force of the drive spring pushes the chassis to retract the syringe carrier relative to the case.

20 Claims, 9 Drawing Sheets

(58) Field of Classification Search
USPC .......................................................... 604/198
See application file for complete search history.

(56) References Cited

FOREIGN PATENT DOCUMENTS

| EP | 0516473 | 5/1992 |
|---|---|---|
| EP | 2399630 | 12/2011 |
| EP | 2438947 | 4/2012 |
| WO | WO2007/129324 | 11/2007 |
| WO | WO 2007/129324 | 11/2007 |
| WO | WO2011/101383 | 8/2011 |
| WO | WO 2011/101383 | 8/2011 |

OTHER PUBLICATIONS

International Preliminary Report on Patentability in International Application No. PCT/EP2012/076097, dated Jun. 24, 2014, 8 pages.
International Search Report in International Application No. PCT/EP2012/076097, dated Apr. 17, 2013.
Written Opinion in International Application No. PCT/EP2012/076097, dated Apr. 17, 2013.

* cited by examiner

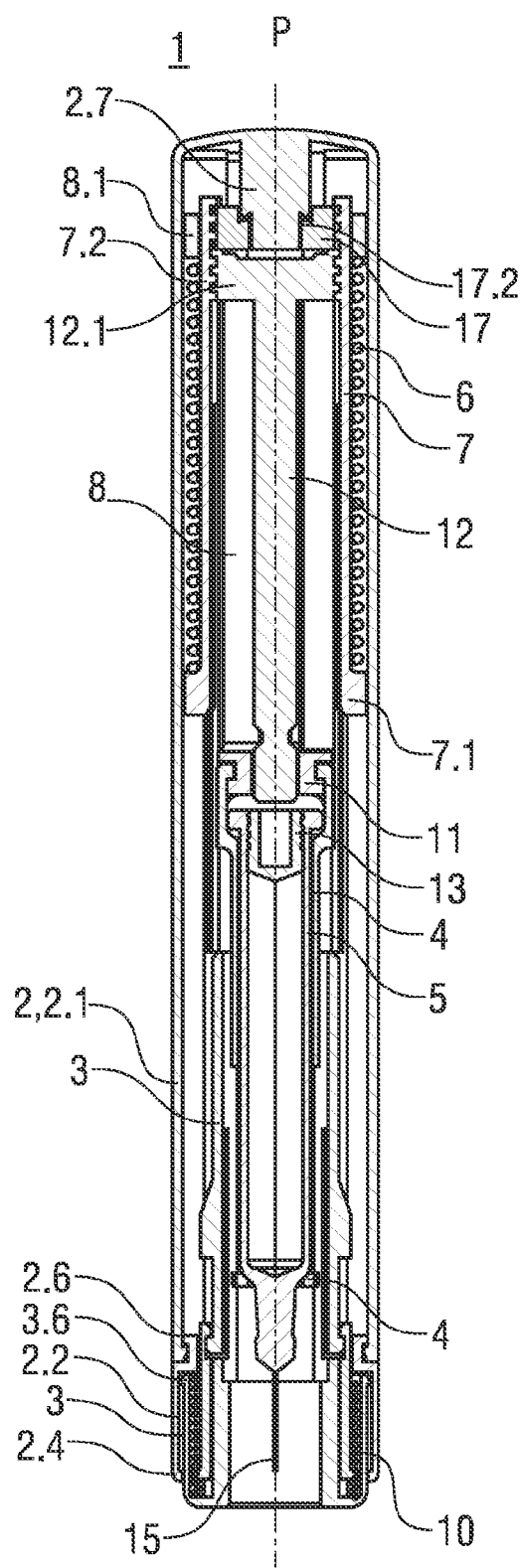
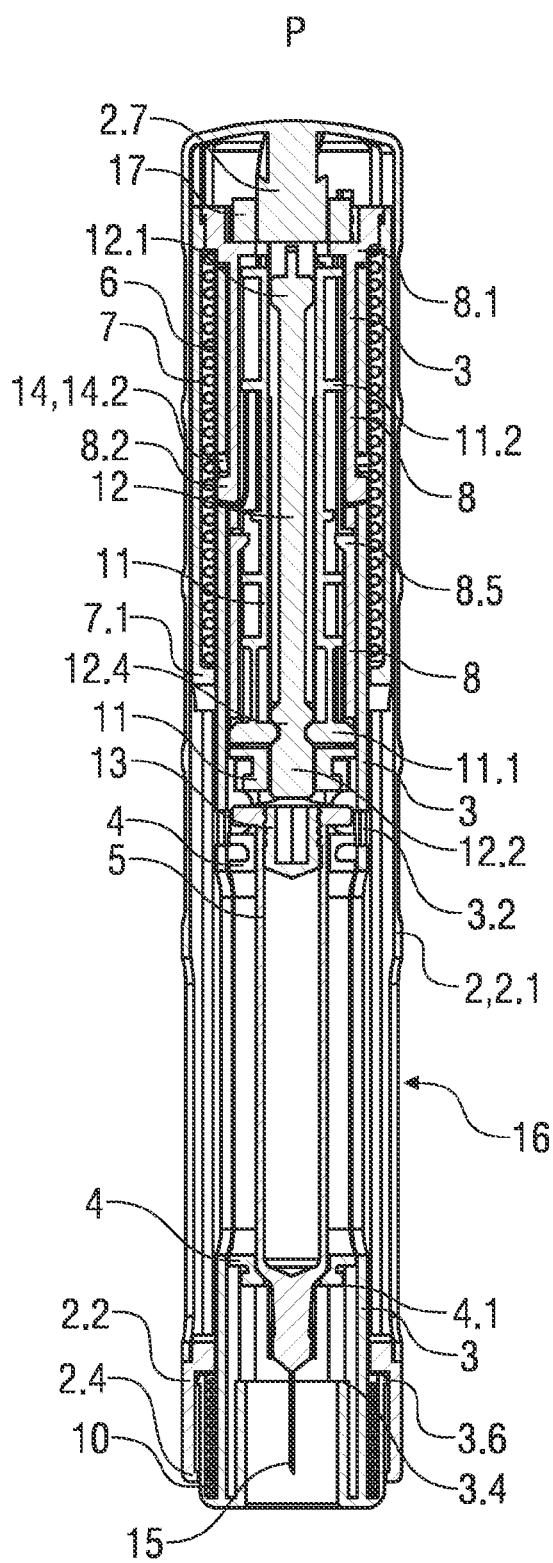
FIG 5A
FIG 5B

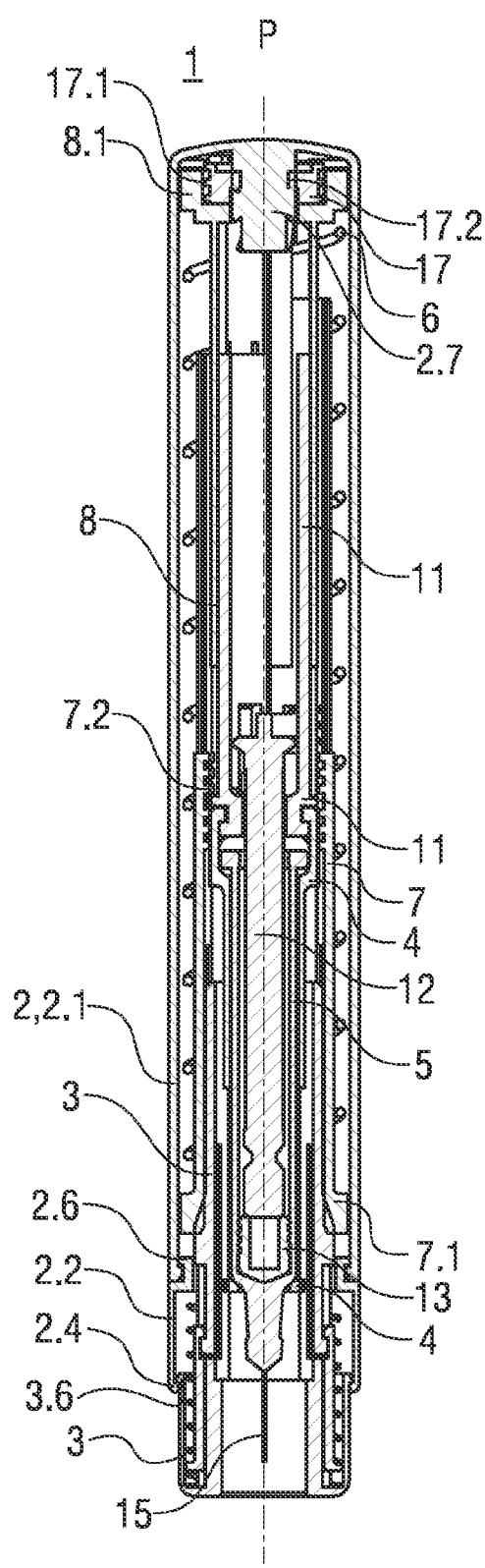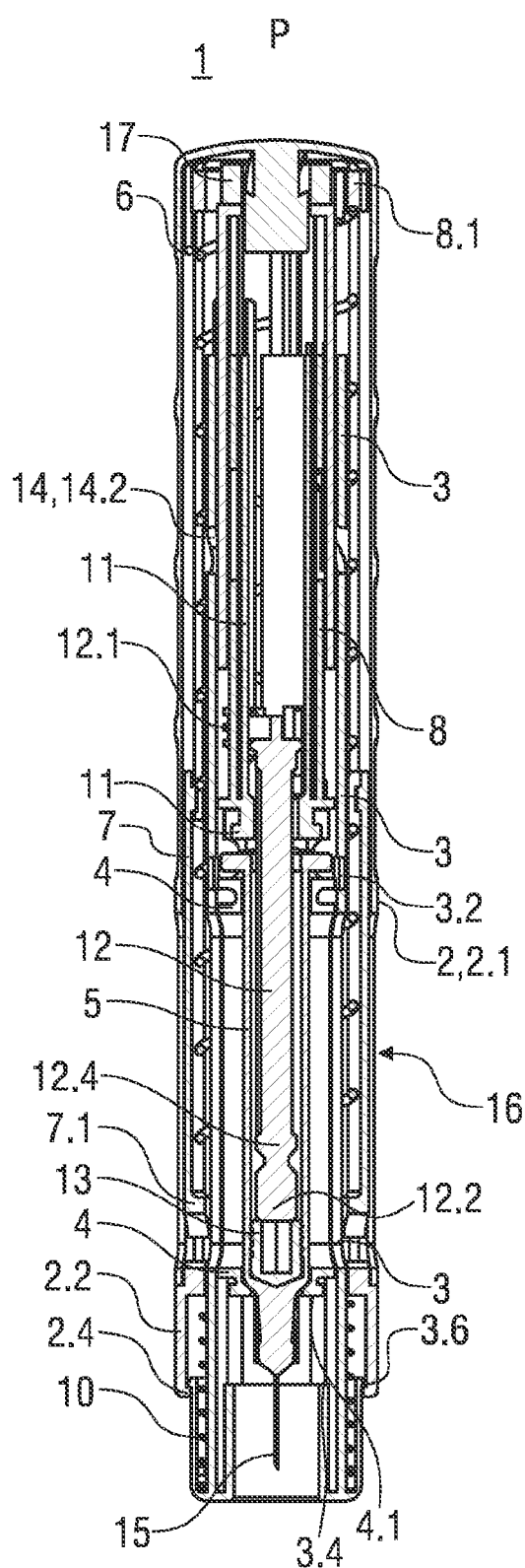
FIG 10A
FIG 10B

AUTOINJECTOR WITH AN INNER PLUNGER WHICH DISENGAGES THE OUTER PLUNGER TO RETRACT THE SYRINGE CARRIER

CROSS REFERENCE TO RELATED APPLICATIONS

The present application is a continuation of U.S. patent application Ser. No. 14/366,868, filed Jun. 19, 2014, which is a U.S. National Phase Application pursuant to 35 U.S.C. § 371 of International Application No. PCT/EP2012/076097, filed Dec. 19, 2012, which claims priority to European Patent Application No. 11194775.0, filed Dec. 21, 2011. The entire disclosure contents of these applications are herewith incorporated by reference into the present application.

TECHNICAL FIELD

The invention relates to an autoinjector for administering a medicament.

BACKGROUND

Administering an injection is a process which presents a number of risks and challenges for users and healthcare professionals, both mental and physical injection devices typically fall into two categories—manual devices and auto-injectors. In a conventional manual device, a user must provide force to drive a medicament through a needle. This is typically done by some form of button/plunger that has to be continuously pressed during the injection. There are numerous disadvantages for the user from this approach. For example, if the user stops pressing the button/plunger, the injection will stop and may not deliver an intended dose to a patient. Further, the force required to push the button/plunger may be too high for the user (e.g., if the user is elderly). And, aligning the injection device, administering the injection and keeping the injection device still during the injection may require dexterity which some patients (e.g., elderly patients, children, arthritic patients, etc.) may not have.

Autoinjector devices aim to make self-injection easier for patients. A conventional autoinjector may provide the force for administering the injection by a spring, and trigger button or other mechanism may be used to activate the injection. Autoinjectors may be single-use or reusable devices.

There remains a need for an improved autoinjector.

SUMMARY

It is an object of the present invention to provide an improved autoinjector.

In an exemplary embodiment, an autoinjector according to the present invention comprises a case, a chassis slidably arranged in the case, a syringe carrier operably coupled to the chassis, an outer plunger selectively engaged to the chassis, an inner plunger selectively engaged to the outer plunger, and a drive spring applying a biasing force to the outer plunger. The biasing force is applied to the inner plunger when the inner plunger is engaged to the outer plunger. Rotation of the chassis causes the inner plunger to rotate relative to the outer plunger and disengage the outer plunger to remove the biasing force from the drive spring on the inner plunger. When the inner plunger disengages the outer plunger, the biasing force of the drive spring pushes the chassis to retract the syringe carrier relative to the case.

In an exemplary embodiment, the autoinjector further comprises a needle shroud slidably arranged in the case. Axial movement of the needle shroud relative to the case causes rotation of the chassis relative to the needle shroud.

In an exemplary embodiment, the autoinjector further comprises a firing nut rotatably disposed on the chassis. The firing nut engages the outer plunger when in a first angular position and disengages the outer plunger when in a second angular position. The case includes a stem adapted to rotate the firing nut from the first angular position to the second angular position. When the firing nut is in the second angular position, the biasing force of the drive spring pushes the outer plunger in a distal direction (D) relative to the case.

In an exemplary embodiment, the needle shroud includes a guide track adapted to engage a pin on the chassis. The pin moves from an angled portion to an axial portion of the guide track causing rotation of the chassis relative to the needle shroud when the needle shroud translates relative to the case.

In an exemplary embodiment, the autoinjector further comprises a coupling carrier coupled to the syringe carrier and selectively engaged to the inner plunger. The coupling carrier includes resilient arms adapted to releasably engage the inner plunger, and the biasing force of the drive spring causes the inner plunger to deflect the resilient arms when a front stop on the syringe carrier abuts a shroud shoulder on the needle shroud. When the resilient arms disengage the inner plunger, the inner plunger is adapted to push a stopper in a syringe. The chassis includes a resilient clip adapted to engage a stop on the coupling carrier. When the biasing force of the drive spring pushes the chassis, the clip engages the stop and retracts the coupling carrier and the syringe carrier relative to the case.

In an exemplary embodiment, the autoinjector further comprises a control spring axially biasing the needle shroud relative to the case.

In an exemplary embodiment, rotation of the chassis relative to the needle shroud causes rotation of the firing nut to a third angular position in which the firing nut is adapted to advance over the stem.

In an exemplary embodiment, the needle shroud includes a resilient non-return clip adapted to engage the case and prevent translation of the needle shroud relative to the case.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein:

FIGS. 5A and 5B show two longitudinal sections of an exemplary embodiment of an autoinjector with a distal end pushed against an injection site according to the present invention, FIGS. 10A and 10B show two longitudinal sections of an exemplary embodiment of an autoinjector removed from an injection site according to the present invention.

Corresponding parts are marked with the same reference symbols in all figures.

DETAILED DESCRIPTION

Figure 1A:
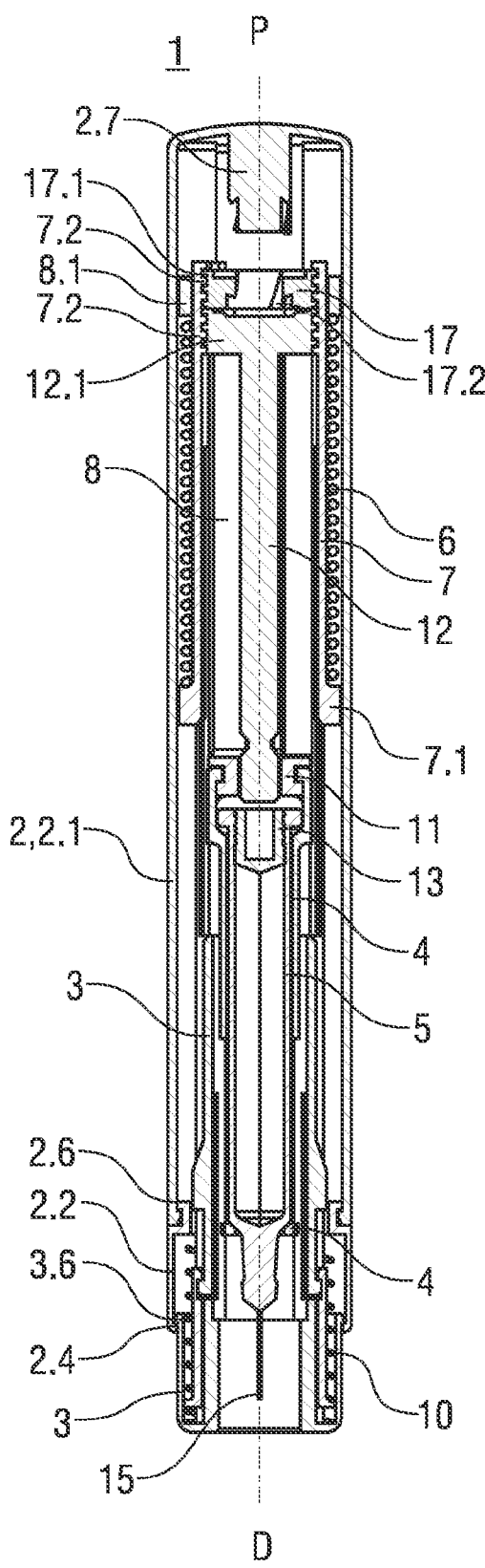
FIGS. 1A and 1B show two longitudinal sections of an exemplary embodiment of an autoinjector in an initial state according to the present invention.
Figure 1B:
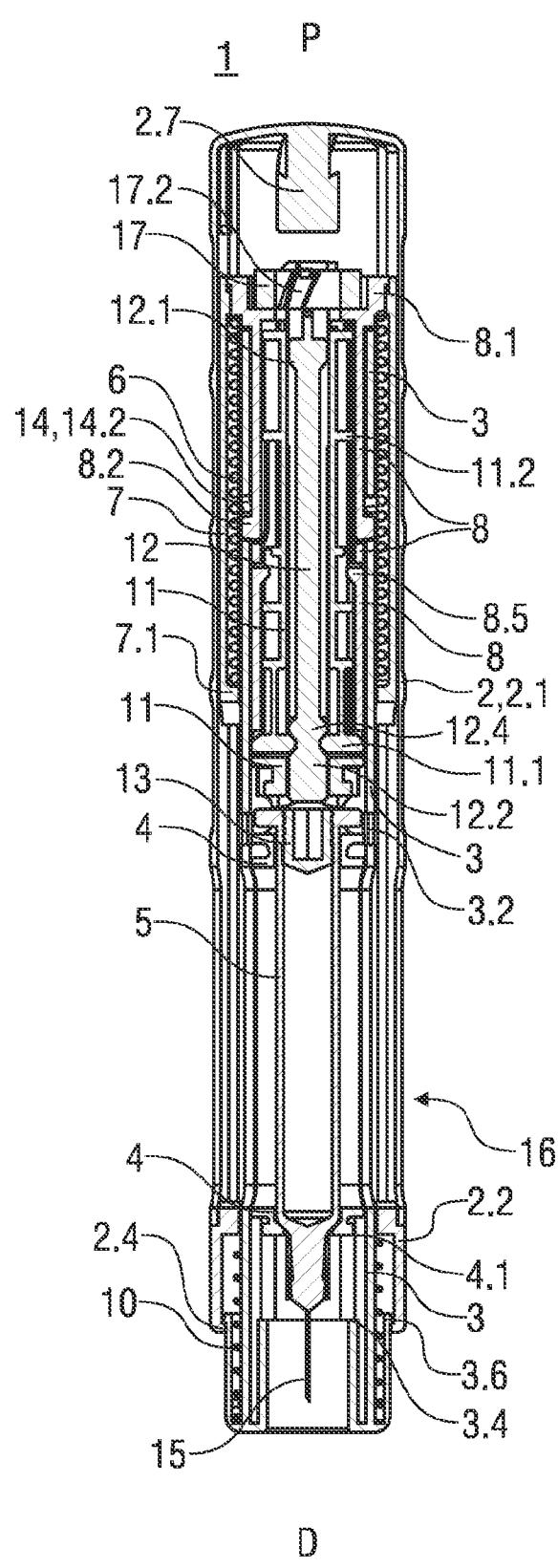
Figure 2:
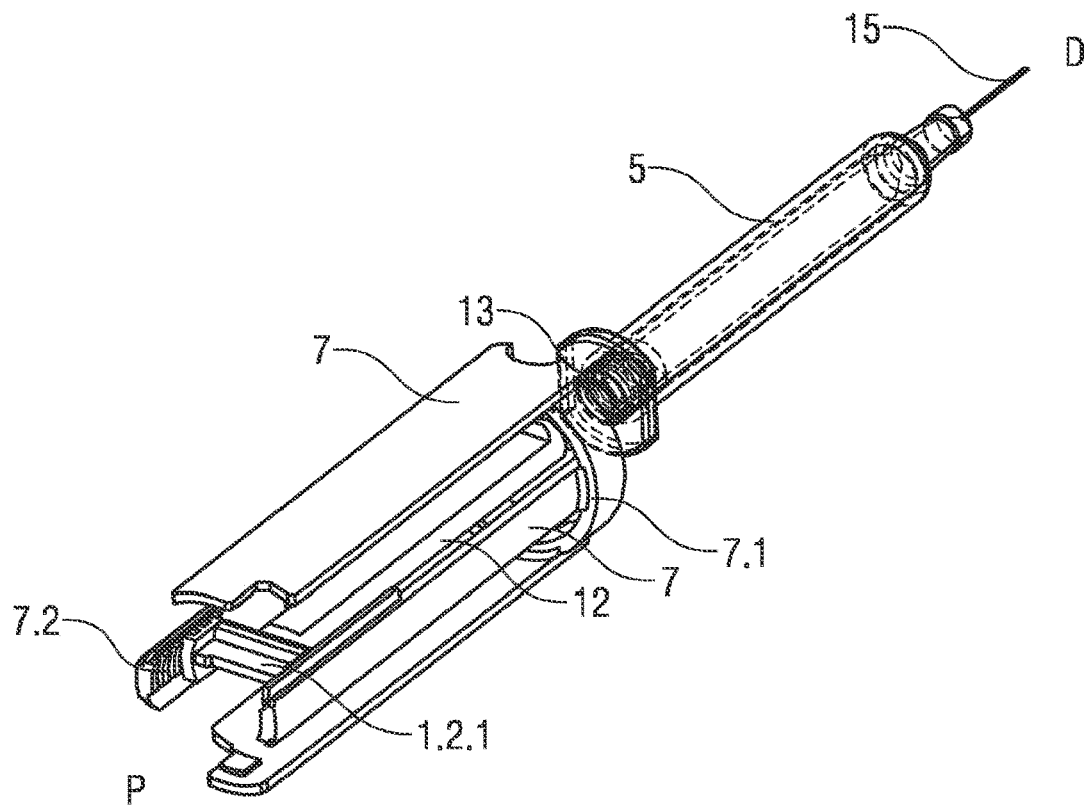
FIG. 2 is a perspective view of exemplary embodiments of a syringe, an inner plunger and an outer plunger for an autoinjector according to the present invention.

FIGS. 1A and 1B show two longitudinal sections of an exemplary embodiment of an autoinjector 1 for delivering a medicament. The sectional planes of the longitudinal sections are essentially oriented perpendicularly with respect to each other.

In an exemplary embodiment, the autoinjector 1 comprises an elongate case 2 comprising a rear case 2.1 coupled to a front case 2.2. A needle shroud 3 is telescopically arranged on the case 2 and may be resiliently coupled to the front case 2.2 by a control spring 10 which applies a biasing force on the needle shroud 3 toward a distal direction D.

A syringe carrier 4 is slidably disposed in the case 2 and is arranged to hold a syringe 5 having a needle 15. As explained further below, the syringe carrier 4 includes an abutment surface 4.1 formed on its distal end that is adapted to abut a shoulder 3.4 formed on the distal portion of the needle shroud 3 when the syringe carrier 4 is moving axially in the distal direction D relative to the needle shroud 3. A distance between a distal face of the needle shroud 3 and the shoulder 3.4 may define the injection depth of the needle 15.

A proximal end of the needle shroud 3 is adapted to abut a chassis 8 which is slidably disposed in the case 2. A collar 8.1 disposed on a proximal end of the chassis 8 acts as a proximal bearing for a drive spring 6, which bears distally on a shoulder 7.1 on an outer plunger 7 that is telescopically arranged on the chassis 8.

Figure 7:
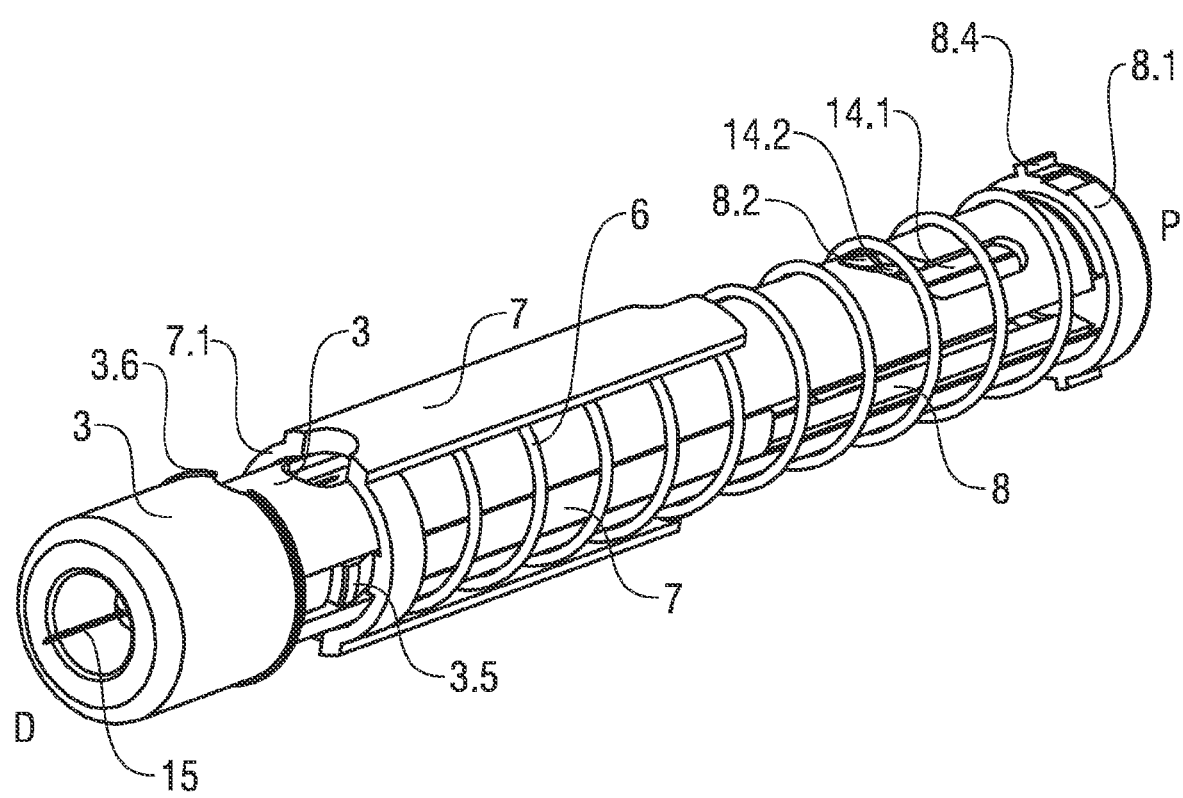
FIG. 7 is a perspective view of exemplary embodiments of internal components of an exemplary embodiment of an autoinjector with a needle extended according to the present invention.

As shown in FIG. 7, in an exemplary embodiment, the collar 8.1 includes a radial protrusion 8.4 which is adapted to prevent rotation of the chassis 8 relative to the rear case 2.1 when the autoinjector 1 is pressed against an injection site. In an exemplary embodiment, the radial protrusion 8.4 is adapted to engage a channel formed in the rear case 2.1, and when the needle shroud 3 is pressed against the injection site, the radial protrusion 8.4 abuts the channel and is prevented from rotating relative to the rear case 2.1. Prior to and after use, the radial protrusion 8.4 does not abut the channel and thus the collar 8.1 (and chassis 8) may rotate relative to the rear case 2.1.

Referring back to FIGS. 1A and 1B, in an exemplary embodiment, a firing nut 17 is selectively engaged to outer plunger 7. The firing nut 17 may rotatably sit in a cavity of the collar 8.1. The firing nut 17 may include teeth 17.1 which are adapted to engage teeth 7.2 formed on a surface of the outer plunger 7. The teeth 17.1 on the firing nut 17 may be formed on a selected portion of the firing nut 17, such that rotation of the firing nut 17 relative to the outer plunger 7 from a first angular position to a second angular position may disengage the outer plunger from the firing nut 17.

The teeth 7.2 of the outer plunger 7 may also engage corresponding teeth 12.1 formed on an inner plunger 12. For example, the inner plunger 12 may include a stem and a transverse element coupled to a proximal portion of the stem, and an outer surface of the transverse element may include the teeth 12.1 for engaging the teeth 7.2 on the outer plunger 7.

Figure 3:
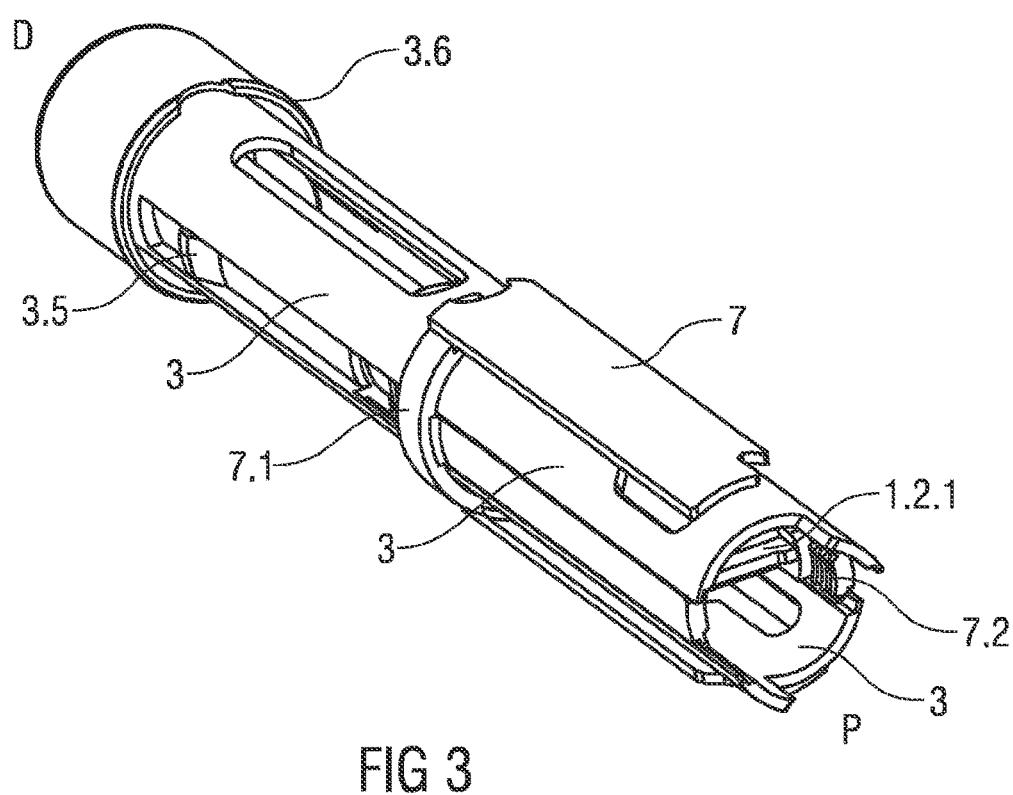
FIG. 3 is a perspective view of an exemplary embodiment of an outer plunger guided in a needle shroud according to the present invention.

As shown in FIG. 3, the outer plunger 7 may be keyed to the needle shroud 3 to allow axial relative movement but prevent rotational relative movement. For example, the outer plunger 7 may include a plurality of legs, and one or more of the legs may be adapted to engage a groove or channel formed in the needle shroud 3.

Referring back to FIGS. 1A and 1B, a coupling carrier 11 is slidably arranged in and keyed to the chassis 8 (allowing for relative translation and joint rotation) and is coupled to the syringe carrier 4. The inner plunger 12 is arranged telescopically in the coupling carrier 11 to allow for axial movement of the inner plunger 12 relative to the coupling carrier 11 and joint rotation with the coupling carrier 11 relative to the chassis 8. Two resilient arms 11.1 on the coupling carrier 11 are arranged to selectively engage a groove between a first plunger shoulder 12.2 and a second plunger shoulder 12.4 on the inner plunger 12 in a manner to couple the inner plunger 12 and the coupling carrier 11 for joint axial translation. In an exemplary embodiment, the resilient arms 11.1 and the first plunger shoulder 12.2 are in a ramped engagement so as to allow the resilient arms 11.1 to deflect radially and disengage the inner plunger 12.

In an exemplary embodiment, the resilient arms 11.1 are maintained in engagement with the first plunger shoulder 12.2, because the needle shroud 3 abuts the resilient arms 11.1. However, the needle shroud 3 includes first apertures 3.2 which, when aligned with the resilient arms 11.1, allow space for the resilient arms 11.1 to deflect radially and disengage the inner plunger 12.

In an exemplary embodiment, a proximal end of the case 2 includes a stem 2.7 extending in the proximal direction and having a thread adapted to engage a corresponding thread 17.2 formed in the firing nut 17. As explained further below, when the thread on the stem 2.7 engages the thread 17.2 on the firing nut 17, the firing nut 17 rotates relative to the outer plunger 7.

In an exemplary embodiment, a cap (not shown) is removably coupled to the front case 2.2 and/or the needle shroud 3. The cap may be coupled to a needle sheath (not illustrated) arranged on the needle 15, and removal of the cap may remove the needle sheath.

FIGS. 1A and 1B show the autoinjector 1 in an initial state, prior to use. Prior to use, the needle shroud 3 extends from the case 2 under the biasing force of the control spring 10 to cover a distal tip of the needle 15. As shown in FIG. 7, in an exemplary embodiment, the needle shroud 3 includes a guide track 14 having an axial portion 14.1 and an angled portion 14.2, and a pin 8.2 on the chassis 8 engages the guide track 14. In the initial state, the pin 8.2 is in a distal portion of the angled section 14.2. Referring back to FIGS. 1A and 1B, the firing nut 17 and the inner plunger 12 are both engaged to the outer plunger 7, and the coupling carrier 11 is engaged to the inner plunger 12.

Figure 4A:
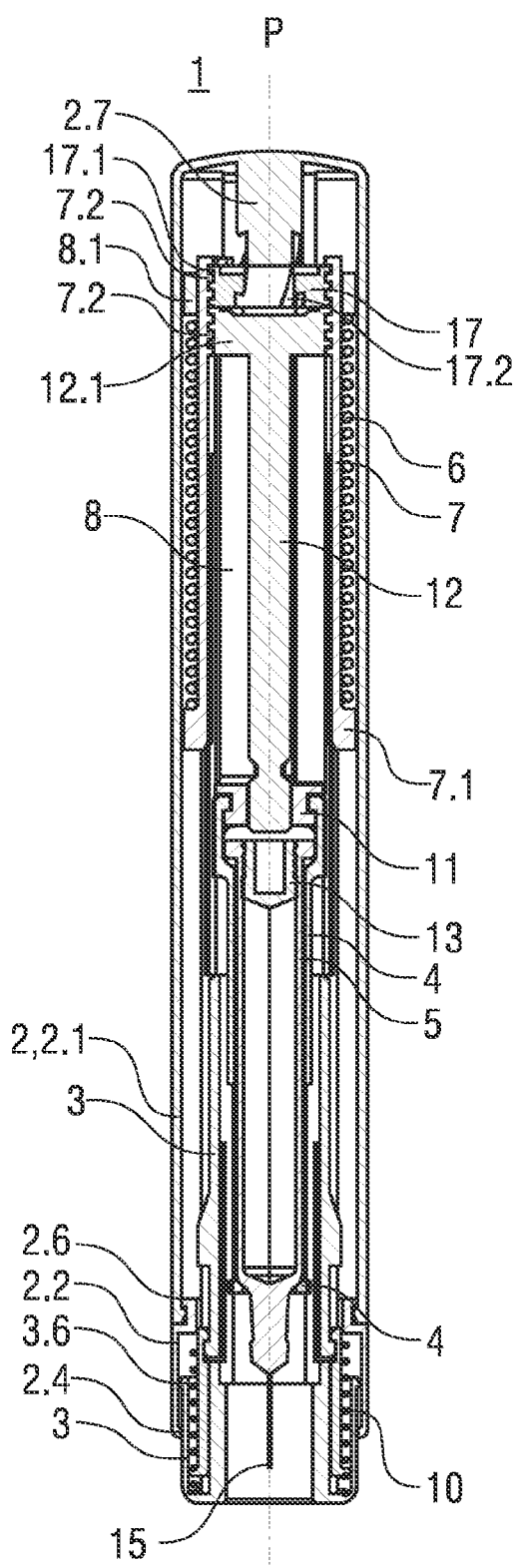
FIGS. 4A and 4B show two longitudinal sections of an exemplary embodiment of an autoinjector with a distal end pushed against an injection site according to the present invention.
Figure 4B:
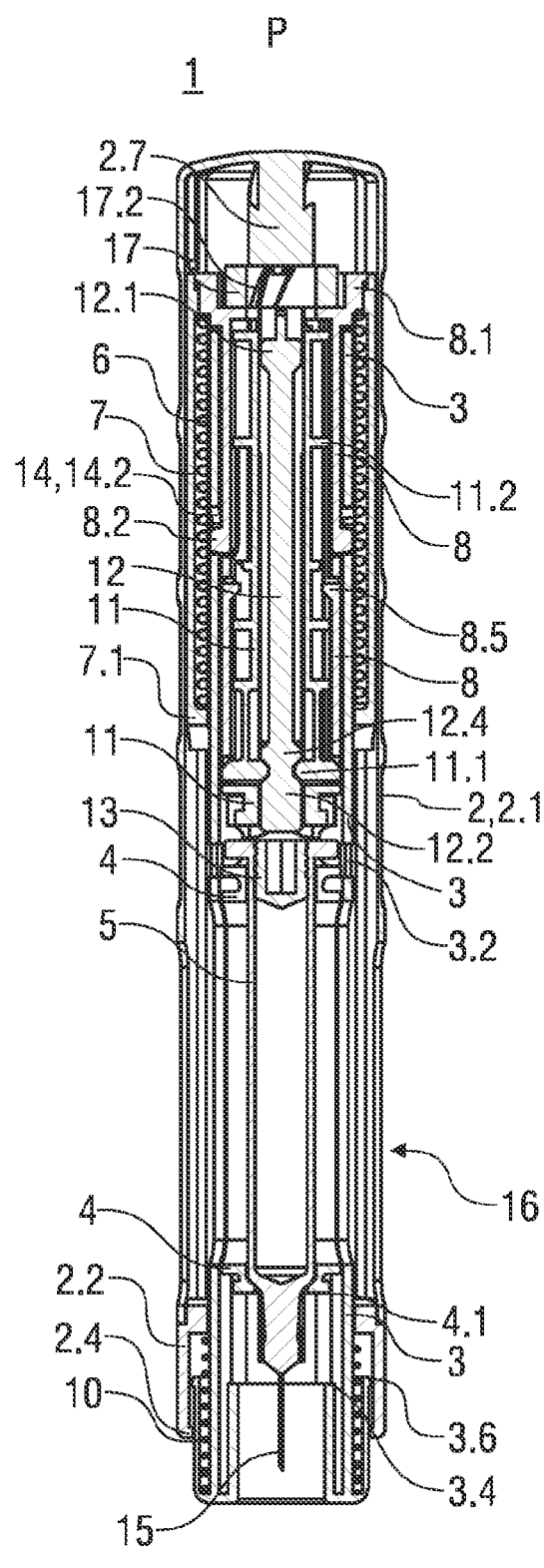

As shown in FIGS. 4A and 4B, when the autoinjector 1 is pressed against an injection site, the needle shroud 3 translates into the case 2 in the proximal direction P, compressing the control spring 10. The needle shroud 3 pushes the chassis 8 in the proximal direction P. Movement of the chassis 8 results in corresponding movement of the firing nut 17 which also results in corresponding movement of the outer plunger 7, since the firing nut 17 is engaged to the outer plunger 7 via teeth 17.1. Since the inner plunger 12 is engaged to the outer plunger 7, the inner plunger 12 and the coupling carrier 11, the syringe carrier 4 and the syringe 5 move in conjunction with the inner plunger 12.

As shown in FIGS. 5A and 5B, the autoinjector 1 is pressed further against the injection site (substantially fully compressing the control spring 10), and the stem 2.7 engages the firing nut 17. As the stem 2.7 engages the firing nut 17, the firing nut 17 rotates from the first angular position to the second angular position, disengaging the outer plunger 7.

Figure 6A:
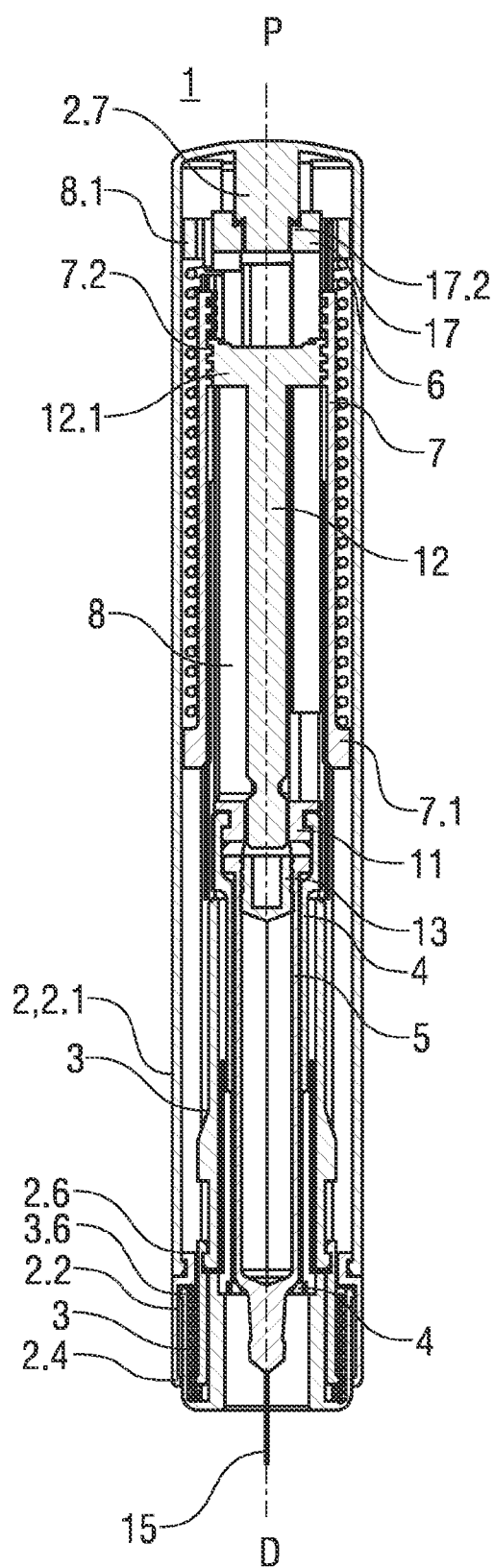
FIGS. 6A and 6B show two longitudinal sections of an exemplary embodiment of an autoinjector with an injection needle extended beyond the distal end according to the present invention.
Figure 6B:
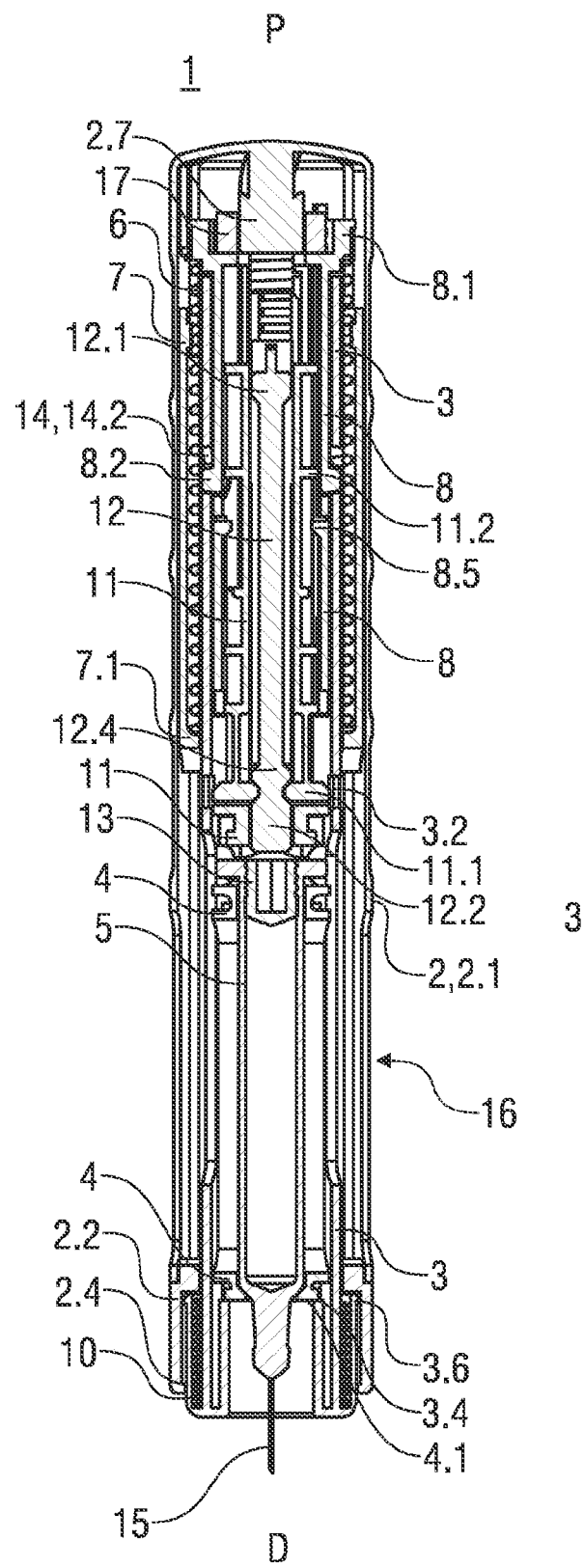

As shown in FIGS. 6A and 6B, when the firing nut 17 rotates into the second angular position, the outer plunger 7 is released from the chassis 8, and the drive spring 6 pushes the outer plunger 7 in the distal direction D. Because the inner plunger 12 is coupled to the outer plunger 7, the inner plunger 12 (and the coupling carrier 11, syringe carrier 4 and syringe 5) moves in the distal direction D. Movement of the syringe carrier 4 in the distal direction D leads to insertion of the needle 15 in the injection site. A penetration depth of the needle 15 is defined by a front stop 4.1 on the syringe carrier 4 abutting an inner distal shroud shoulder 3.4 on the needle shroud 3.

Figure 8A:
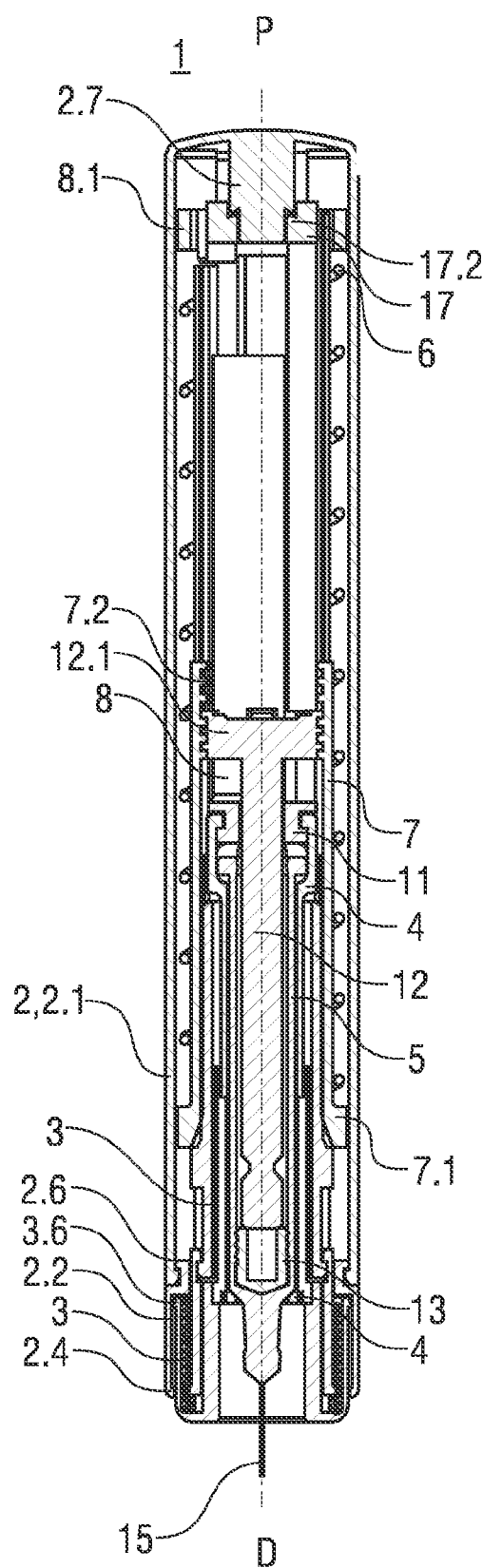
FIGS. 8A and 8B show two longitudinal sections of an exemplary embodiment of an autoinjector after an injection according to the present invention.
Figure 8B:
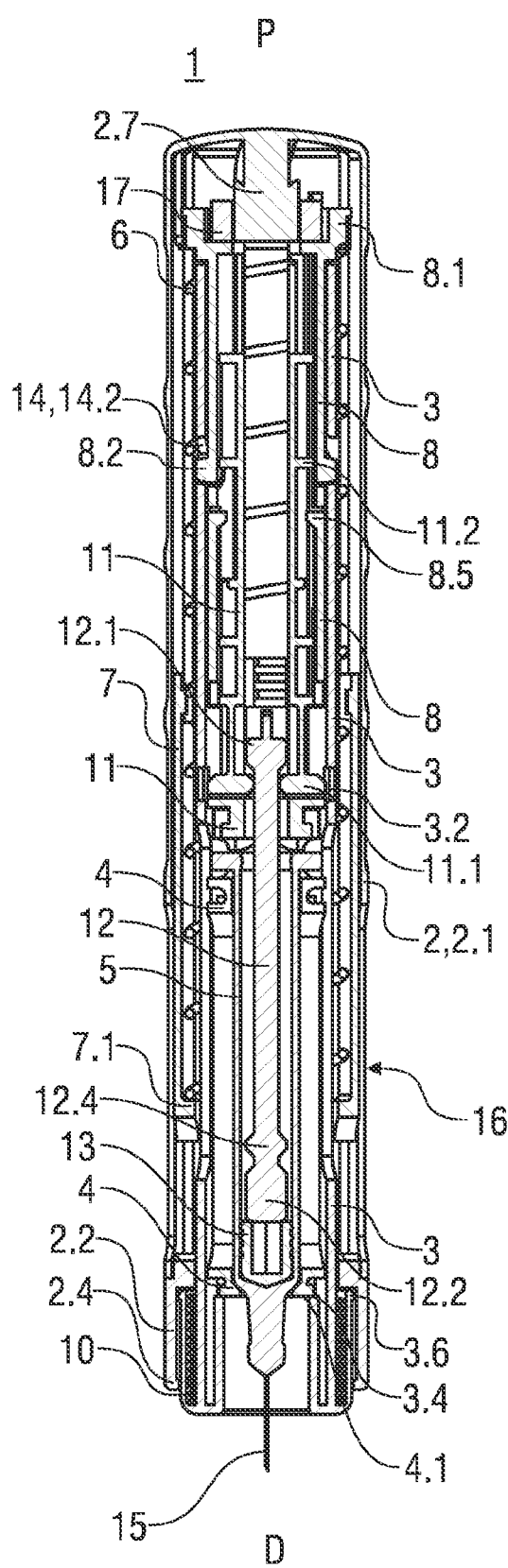

As shown in FIGS. 8A and 8B, when the front stop 4.1 on the syringe carrier 4 abuts the inner distal shroud shoulder 3.4 on the needle shroud 3, the resilient arms 11.1 of the coupling carrier 11 align with the first apertures 3.2 of the needle shroud 3, and the force of the drive spring 6 causes the first plunger shoulder 12.2 to deflect the resilient arms 11.1 of the coupling carrier 11 into the first apertures 3.2. When the resilient arms 11.1 are deflected, the inner plunger 12 moves in the distal direction D relative to the coupling carrier 11. The inner plunger 12 abuts a stopper 13 in the syringe 5 and pushes the stopper 13 in the distal direction D to expel the medicament from the needle 15.

Figure 9A:
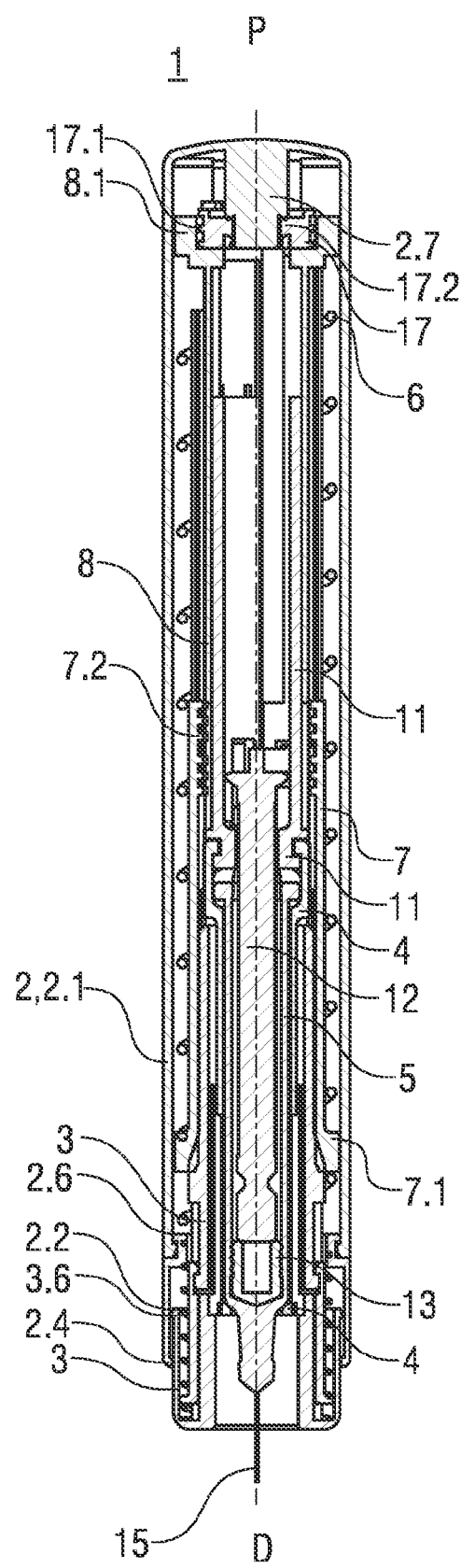
FIGS. 9A and 9B show two longitudinal sections of an exemplary embodiment of an autoinjector removed from an injection site according to the present invention.
Figure 9B:
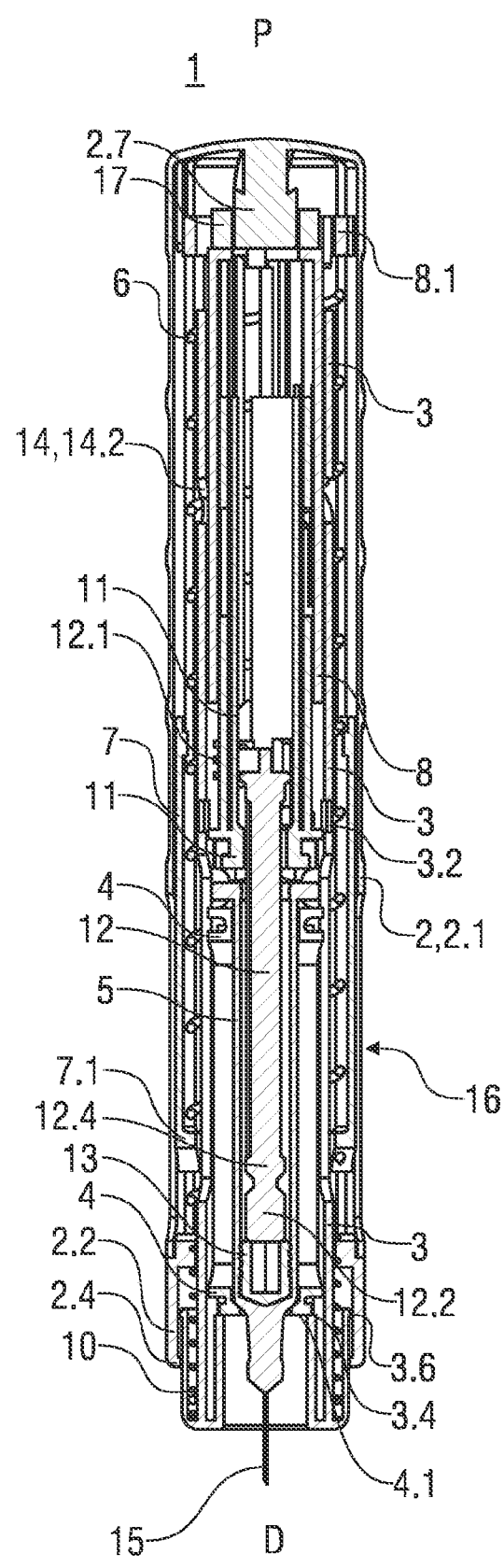

As shown in FIGS. 9A and 9B, when the autoinjector 1 is removed from the injection site after an injection is complete or during the injection, the biasing force of the control spring 10 causes the needle shroud 3 to translate in the distal direction D relative to the case 2. Under the force of the drive spring 6, the outer plunger 7 translates in the distal direction D relative to the case 2. As the needle shroud 3 translates in the distal direction D relative to the case 2, the engagement of the pin 8.2 on the chassis 8 and the guide track 14 causes the chassis 8 to rotate relative to the case 2. As the needle shroud 3 translates, the geometry of the guide track 14 causes the pin 8.2 to move through the angled portion 14.2 of the guide track 14 causing rotation of the chassis 8 relative to the needle shroud 3 and into the axial portion 14.1 of the guide track 14 which allows for axial movement of the needle shroud 3 relative to the chassis 8. Because the outer plunger 7 is keyed to the needle shroud 3, the chassis 8 rotates relative to the outer plunger 7 and causes rotation of the coupling carrier 11 which, in turn, rotates the inner plunger 12 to disengage from the outer plunger 7. Thus, the teeth 12.1 on the inner plunger 12 disengage the teeth 7.2 on the outer plunger 7. Further, extension of the needle shroud 3 relative to the case 2 is limited by the pin 8.2 abutting the proximal end of the axial portion 14.1 of the guide track 14 during translation of the needle shroud 3.

When the inner plunger 12 disengages the outer plunger 7, the force of the drive spring 6 does not act on the inner plunger 12. Thus, even if the autoinjector 1 is removed from the injection site during the injection, the expulsion of the medicament from the syringe 5 will stop, because there is no force to move the inner plunger 12 (and the stopper 13).

As the insertion depth of the needle 15 is defined by the syringe carrier 4 contacting the needle shroud 3, allowing the needle shroud 3 to re-advance on removal from the injection site could also allow the syringe 5 to advance further. In order to avoid this, one or more resilient clips 8.5 are arranged on the chassis 8 to engage a stop 11.2 on the coupling carrier 11 at the end of the rotation of the chassis 8. The clips 8.5 prevents the coupling carrier 11 (and the syringe carrier 4 coupled thereto and the syringe 5) from advancing in the distal direction D after the autoinjector 1 has been removed from the injection site.

FIGS. 10A and 10B show the needle shroud 3 in its extended state and the syringe carrier 4 (and the syringe 5) in a retracted state. In an exemplary embodiment, when the chassis 8 rotates by movement of the guide pin 8.2 in the guide track 14, the firing nut 17 rotates to a third angular position and disengages the thread on the stem 2.7 (which was preventing movement of the firing nut 17 in the proximal direction P relative to the stem 2.7), allowing the firing nut 17 and the collar 8.1 to be pushed in the proximal direction P against the proximal end of the case 2 under the force of the drive spring 6. In another exemplary embodiment, the force of the drive spring 6 pushes the collar 8.1 in the proximal direction P causing the firing nut 17 to rotate to the third angular position and disengages the thread on the stem 2.7 (or, alternatively, follows the thread on the stem 2.7 until it abuts the proximal end of the case). The proximal movement of the collar 8.1 causes a proximal movement of the chassis 8, the coupling carrier 11 and the syringe carrier 4, which retracts the syringe 5 and the needle 15 in the proximal direction P relative to the case 2. For example, the stop 11.2 on the coupling carrier 11 may engage the clip 8.5 on the chassis 8, such that the proximal movement of the chassis 8 may result in a corresponding proximal movement of the coupling carrier 11. The residual force in the drive spring 6 may maintain the syringe 5 in a retracted position relative to the case 5.

Hooks 3.6 on a distal end of the needle shroud 3 may engage a distal case shoulder 2.4 to limit extension of the needle shroud 3 relative to the case 2 under the force of the control spring 10.

In an exemplary embodiment, a resilient non-return clip (not shown) may be arranged on the needle shroud 3 and adapted to engage the case 2 after the needle shroud 3 has been extended. The non-return clip may prevent the needle shroud 3 from moving in the proximal direction P relative to the case 2 if the autoinjector 1 is pressed against a subsequent injection site or during handling after an injection.

In an exemplary embodiment, a viewing window 16 is arranged in the case 2 for inspecting contents of the syringe 5.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4 (1-39)-NH2,
H-(Lys)5-des Pro36, des Pro37 Exendin-4 (1-39)-NH2,
des Pro36 Exendin-4 (1-39),
des Pro36 [Asp28] Exendin-4 (1-39),
des Pro36 [IsoAsp28] Exendin-4 (1-39),
des Pro36 [Met(O)14, Asp28] Exendin-4 (1-39),
des Pro36 [Met(O)14, IsoAsp28] Exendin-4 (1-39),
des Pro36 [Trp(O2)25, Asp28] Exendin-4 (1-39),
des Pro36 [Trp(O2)25, IsoAsp28] Exendin-4 (1-39),
des Pro36 [Met(O)14 Trp(O2)25, Asp28] Exendin-4 (1-39),
des Pro36 [Met(O)14 Trp(O2)25, IsoAsp28] Exendin-4 (1-39); or
des Pro36 [Asp28] Exendin-4 (1-39),
des Pro36 [IsoAsp28] Exendin-4 (1-39),
des Pro36 [Met(O)14, Asp28] Exendin-4 (1-39),
des Pro36 [Met(O)14, IsoAsp28] Exendin-4 (1-39),
des Pro36 [Trp(O2)25, Asp28] Exendin-4 (1-39),
des Pro36 [Trp(O2)25, IsoAsp28] Exendin-4 (1-39),
des Pro36 [Met(O)14 (O2)25, Asp28] Exendin-4 (1-39),
des Pro36 [Met(O)14 (O2)25, IsoAsp28] Exendin-4 (1-39),
wherein the group -Lys6-NH2 may be bound to the C-terminus of the Exendin-4 derivative;
or an Exendin-4 derivative of the sequence
des Pro36 Exendin-4 (1-39)-Lys6-NH2 (AVE0010),
H-(Lys)6-des Pro36 [Asp28] Exendin-4(1-39)-Lys6-NH2
des Asp28 Pro36, Pro37, Pro38Exendin-4(1-39)-NH2
H-(Lys)6-des Pro36, Pro38 [Asp28] Exendin-4(1-39)-NH2
H-Asn-(Glu)5des Pro36, Pro37, Pro38 [Asp28] Exendin-4 (1-39)-NH2
des Pro36, Pro37, Pro38 [Asp28] Exendin-4(1-39)-(Lys)6-NH2
H-(Lys)6-des Pro36, Pro37, Pro38 [Asp28] Exendin-4 (1-39)-(Lys)6-NH2
H-Asn-(Glu)5-des Pro36, Pro37, Pro38 [Asp28] Exendin-4 (1-39)-(Lys)6-NH2
H-(Lys)6-des Pro36 [Trp(O2)25, Asp28] Exendin-4 (1-39)-Lys6-NH2
H-des Asp28 Pro36, Pro37, Pro38 [Trp(O2)25] Exendin-4 (1-39)-NH2
H-(Lys)6-des Pro36, Pro37, Pro38 [Trp(O2)25, Asp28] Exendin-4 (1-39)-NH2
H-Asn-(Glu)5-des Pro36, Pro37, Pro38 [Trp(O2)25, Asp28] Exendin-4 (1-39)-NH2
des Pro36, Pro37, Pro38 [Trp(O2)25, Asp28] Exendin-4 (1-39)-(Lys)6-NH2
H-(Lys)6-des Pro36, Pro37, Pro38 [Trp(O2)25, Asp28] Exendin-4 (1-39)-(Lys)6-NH2
H-Asn-(Glu)5-des Pro36, Pro37, Pro38 [Trp(O2)25, Asp28] Exendin-4 (1-39)-(Lys)6-NH2
H-(Lys)6-des Pro36 [Met(O)14, Asp28] Exendin-4 (1-39)-Lys6-NH2
des Met(O)14 Asp28Pro36, Pro37, Pro38 Exendin-4 (1-39)-NH2
H-(Lys)6-desPro36, Pro37, Pro38 [Met(O)14, Asp28] Exendin-4 (1-39)-NH2
H-Asn-(Glu)5-des Pro36, Pro37, Pro38 [Met(O)14, Asp28] Exendin-4 (1-39)-NH2
des Pro36, Pro37, Pro38 [Met(O)14, Asp28] Exendin-4 (1-39)-(Lys)6-NH2
H-(Lys)6-des Pro36, Pro37, Pro38 [Met(O)14, Asp28] Exendin-4 (1-39)-(Lys)6-NH2
H-Asn-(Glu)5 des Pro36, Pro37, Pro38 [Met(O)14, Asp28] Exendin-4 (1-39)-(Lys)6-NH2
H-Lys6-des Pro36 [Met(O)14, Trp(O2)25, Asp28] Exendin-4 (1-39)-Lys6-NH2
H-des Asp28Pro36, Pro37, Pro38 [Met(O)14, Trp(O2)25] Exendin-4 (1-39)-NH2
H-(Lys)6-des Pro36, Pro37, Pro38 [Met(O)14, Asp28] Exendin-4 (1-39)-NH2
H-Asn-(Glu)5-des Pro36, Pro37, Pro38 [Met(O)14, Trp(O2) 25, Asp28] Exendin-4 (1-39)-NH2
des Pro36, Pro37, Pro38 [Met(O)14, Trp(O2)25, Asp28] Exendin-4 (1-39)-(Lys)6-NH2
H-(Lys)6-des Pro36, Pro37, Pro38 [Met(O)14, Trp(O2)25, Asp28] Exendin-4 (S1-39)-(Lys)6-NH2, H-Asn-(Glu)5-des Pro36, Pro37, Pro38 [Met(O)14, Trp(O2) 25, Asp28] Exendin-4 (1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, β and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ, and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

The invention claimed is:

1. An autoinjector comprising:
   a case having a distal end and a proximal end;
   a plunger positioned within the case;
   a drive spring positioned within the case applying a biasing force in a distal direction to the plunger;
   a firing nut positioned within the case, the firing nut coupled to the plunger, the firing nut rotatable between a first angular position and a second angular position; and
   a needle shroud slidably arranged in the case, wherein proximal movement of the needle shroud relative to the case causes the firing nut to rotate from the first angular position to the second angular position to release the plunger.

2. The autoinjector of claim 1, wherein the firing nut comprises first teeth, and wherein the plunger comprises second teeth configured to engage the first teeth.

3. The autoinjector of claim 2, wherein the first teeth are configured to disengage the second teeth in response to the firing nut rotating from the first angular position to the second angular position.

4. The autoinjector of claim 2, wherein the case comprises a stem configured to rotate the firing nut from the first angular position to the second angular position.

5. The autoinjector of claim 4, wherein the stem comprises a first thread, and wherein the firing nut comprises a second thread configured to engage the first thread causing the firing nut to rotate relative to the plunger.

6. The autoinjector of claim 1, further comprising a collar disposed on a proximal end of the chassis and configured to act as a proximal bearing for the drive spring.

7. The autoinjector of claim 6, wherein the collar comprises a cavity in which the firing nut sits.

8. The autoinjector of claim 1, wherein the plunger is an outer plunger, and wherein the autoinjector comprises an inner plunger selectively engaged to the outer plunger, wherein the biasing force of the drive spring is applied to the inner plunger when the inner plunger is engaged to the outer plunger.

9. The autoinjector of claim 8, wherein the inner plunger comprises:
a stem; and
a transverse element coupled to a proximal portion of the stem, wherein an outer surface of the transverse element comprises third teeth configured to engage the second teeth of the outer plunger.

10. The autoinjector of claim 1, further comprising a needle shroud slidably arranged in the case, wherein axial movement of the needle shroud relative to the case causes rotation of the chassis relative to the needle shroud.

11. The autoinjector of claim 10, wherein the plunger and the needle shroud are coupled to allow axial relative movement and prevent rotational relative movement.

12. The autoinjector of claim 10, wherein the needle shroud comprises a groove, and wherein the plunger comprises at least one leg configured to engage the groove.

13. The autoinjector of claim 10, wherein the needle shroud comprises a guide track comprising an axial portion and an angled portion, wherein the chassis comprises a pin configured to engage the guide track in response to the needle shroud translating in the distal direction relative to the case, wherein an engagement of the pin and the guide track causes the chassis to rotate relative to the case.

14. The autoinjector of claim 1, further comprising a syringe containing a medicament.

15. A method implemented by an autoinjector comprising a case, a plunger, a drive spring, a firing nut and a needle shroud, the method comprising:
receiving, by the needle shroud slidably arranged in the case having a distal end and a proximal end, a force at a distal end of the needle shroud;
in response to receiving the force at the distal end, proximally moving, by the needle shroud, toward the distal end of the case, wherein the plunger is positioned within the case, and the drive spring is positioned within the case applying a biasing force in a distal direction to the plunger;
in response to the needle shroud proximally moving toward the distal end of the case, rotating, by the firing nut positioned within the case, from a first angular position to a second angular position; and
in response to rotating, by the firing nut, from the first angular position to the second angular position, driving, by the drive spring, the plunger in the distal direction.

16. The method of claim 15, wherein the autoinjector comprises a control spring applying a biasing force on the needle shroud toward the distal direction, wherein receiving the proximal movement by the needle shroud comprises compressing, by the control spring, in response to receiving the proximal movement.

17. The method of claim 16, further comprising:
extending, by the control spring, in response to a removal of the force at the distal end of the needle shroud;
in response to extending by the control spring, moving, by the needle shroud, in the distal direction; and
engaging, by the needle shroud, the case, the engaging preventing translation of the needle shroud in the proximal direction.

18. The method of claim 15, wherein the autoinjector comprises a syringe and a needle, the syringe containing a medicament to be expelled through the needle, wherein the plunger abuts a stopper in the syringe, wherein the method further comprises, in response to driving, by the drive spring, the plunger in the distal direction, pushing, by the plunger, the stopper in the syringe to expel the medicament through the needle.

19. A method comprising:
in an autoinjector comprising:
a case having a distal end and a proximal end,
a plunger positioned within the case,
a drive spring positioned within the case applying a biasing force in a distal direction to the plunger,
a firing nut positioned within the case, the firing nut coupled to the plunger, the firing nut rotatable between a first angular position and a second angular position, and
a needle shroud slidably arranged in the case:
proximally moving the needle shroud relative to the case;
in response to proximally moving the needle shroud relative to the case, rotating the firing nut from the first angular position to the second angular position; and
in response to rotating the firing nut from the first angular position to the second angular position, releasing the plunger.

20. The method of claim 19, wherein the autoinjector comprises a syringe and a needle, the syringe containing a medicament to be expelled through the needle, wherein the plunger abuts a stopper in the syringe, wherein the method further comprises, in response to releasing the plunger, pushing, by the plunger, the stopper in the syringe to expel the medicament through the needle.

* * * * *